United States Patent [19]

Arabori et al.

[11] Patent Number: 5,028,255
[45] Date of Patent: Jul. 2, 1991

[54] N-SUBSTITUTED-3-[(2,3-DIMETHYL-MALEIMIDO)AMINO)]-BENZENESULFONAMIDE DERIVATIVES, HEBICIDAL COMPOSITIONS AND METHOD OF USE

[75] Inventors: Hideo Arabori; Shiro Yamazaki; Masato Arahira; Aiko Murakami, all of Iwaki, Japan

[73] Assignee: Kureha Kagaku Kogyo K.K., Japan

[21] Appl. No.: 473,808

[22] Filed: Feb. 2, 1990

[30] Foreign Application Priority Data

Feb. 20, 1989 [JP] Japan ................................. 1-38396

[51] Int. Cl.⁵ ..................... A01N 43/36; C07D 403/10
[52] U.S. Cl. ....................................... 71/72; 544/331; 544/211; 71/93
[58] Field of Search ..................... 544/298, 331; 71/92

[56] References Cited

U.S. PATENT DOCUMENTS

| | | | |
|---|---|---|---|
| Re. 33,125 | 12/1989 | Campbell et al. | 544/298 |
| 4,424,073 | 1/1984 | Levitt | 544/331 |
| 4,473,394 | 9/1984 | Budzinski et al. | 544/331 |
| 4,565,567 | 1/1986 | Levitt | 544/331 |
| 4,666,506 | 5/1987 | Hillemann | 544/331 |
| 4,685,961 | 8/1987 | Topfl et al. | 544/331 |
| 4,801,327 | 1/1989 | Christensen | 544/331 |
| 4,830,662 | 5/1989 | Levitt | 544/331 |
| 4,833,249 | 5/1989 | Abou-Gharbia | 544/331 |

FOREIGN PATENT DOCUMENTS 116518 8/1984 European Pat. Off. .
162723 11/1985 European Pat. Off. .

*Primary Examiner*—David B. Springer
*Attorney, Agent, or Firm*—Lowe, Price, LeBlanc & Becker

[57] ABSTRACT

Disclosed herein are N-substituted-3-[(2,3-dimethylmaleimido) amino]benzenesulfonamide derivatives of the formula (I):

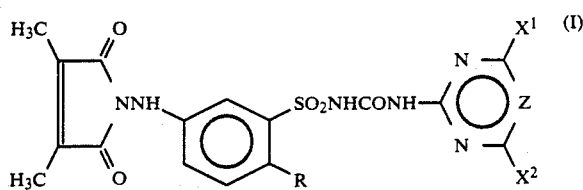

wherein R is Cl, $C_1$–$C_3$ alkyl or $C_1$–$C_4$ alkoxycarbonyl; Z is CH or N; $X^1$ is Cl or $C_1$–$C_3$ alkoxy; and $X^2$ is $C_1$–$C_3$ alkyl or $C_1$–$C_3$ alkoxyl, a process for the preparation thereof, and herbicidal compositions containing the N-substituted-3-[(2,3-dimethylmaleimido) amino]benzenesulfonamide derivatives as active ingredients.

5 Claims, No Drawings

N-SUBSTITUTED-3-[(2,3-DIMETHYL-MALEIMIDO)AMINO)]-BENZENESULFONA-MIDE DERIVATIVES, HEBICIDAL COMPOSITIONS AND METHOD OF USE

BACKGROUND OF THE INVENTION

1) Field of the Invention

The present invention relates to N-substituted-3-[(2,3-dimethylmaleimido)amino]benzenesulfonamide derivatives, a preparation process thereof, and herbicidal compositions containing the derivatives as active ingredients.

2) Description of the Related Art

Numerous compounds have heretofore been proposed as herbicides. Regarding N-substituted benzenesulfonamide derivatives, a variety of compounds has also been reported as herbicides.

For example, EP-A-116518 and Japanese Patent Application Laid-Open (KOKAI) No. 129276/1987 disclose the use of N-(phenylsulfonyl)-N'-pyrimidyl- or triazinyl urea derivatives, which have one or more substituents on the phenyl nucleus, as herbicides. Illustrative of the substituent on the 3-position of the phenyl nucleus include various groups such as $NHCH_3$, $OCH_2CF_3$ and $SCH_2CF_3$.

There have conventionally been strong demands for herbicides capable of exhibiting reliable herbicidal activity even at such low application dosages as bringing about the advantage of reducing the amount present in the environment, herbicides capable of exhibiting selectivity between crops and weeds irrespective of variations in environmental conditions, herbicides free from crop injury to the second crop in double cropping, etc. The present invention has been completed with a view toward meeting such demands.

The present inventors have found, as a result of an investigation, that a series of compounds still unreported in any publications known to the inventors and having a chemical structure different from the compounds disclosed in EP-A-116518 and Japanese Patent Application Laid-Open (KOKAI) No. 129276/1987 referred to above.

SUMMARY OF THE INVENTION

Therefore, an object of the invention is to provide novel compounds which show excellent herbicidal activity.

Another object of the invention is to provide a process for preparing novel compounds which show excellent herbicidal activity.

A further object of the invention is to provide intermediates useful in the preparation of novel compounds which show excellent herbicidal activity.

A still further object of the invention is to provide novel herbicidal compositions which show excellent herbicidal activity.

A still further object of the invention is to provide a method for controlling monocotyledonous or dicotyledonous weeds on an agricultural or nonagricultural land.

In one aspect of the invention, there is thus provided An N-substituted-3-[(2,3-dimethylmaleimido)amino]-benzenesulfonamide derivative of the formula (I):

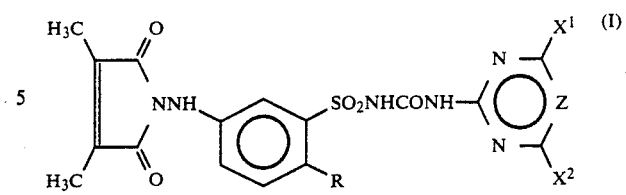

wherein R is Cl, $C_1$-$C_3$ alkyl or $C_1$-$C_4$ alkoxycarbonyl; Z is CH or N; $X^1$ is Cl or $C_1$-$C_3$ alkoxyl; and $X^2$ is $C_1$-$C_3$ alkyl or $C_1$-$C_3$ alkoxyl.

In another aspect of the invention, there is also provided a process for the preparation of an N-substituted-3-[(2,3-dimethylmaleimido)amino]benzenesulfonamide derivative of claim 1, which comprises reacting a 3-[(2,3-dimethylmaleimido)amino]benzenesulfonamide derivative of the formula (II):

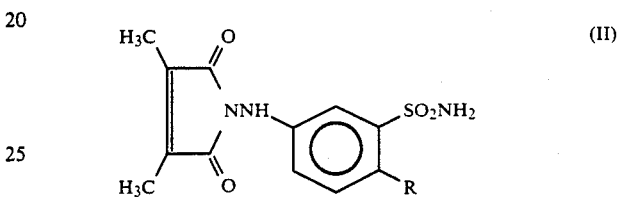

wherein R is Cl, $C_1$-$C_3$ alkyl or $C_1$-$C_3$ alkoxycarbonyl, with a phenylcarbamate derivative of the following formula (III):

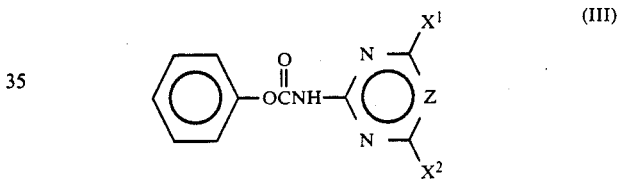

wherein Z is CH or N, $X^1$ is Cl or $C_1$-$C_3$ alkoxyl, and $X^2$ is $C_1$-$C_3$ alkyl or $C_1$-$C_3$ alkoxyl.

In a further aspect of the invention, there is also provided a 3-[(2,3-dimethylmaleimido)amino]benzenesulfonamide derivative useful as an intermediate in the preparation of the above N-substituted-3-[(2,3-dimethylmaleimido)amino]benzenesulfonamide, which is represented by the following formula (II).

In a still further aspect of the invention, there is also provided a herbicidal composition comprising a herbicidally effective amount of an N-substituted-3-[(2,3-dimethylmaleimido)amino]benzenesulfonamide derivative of the formula (I) and an agronomically-acceptable vehicle or diluent.

In a still further aspect of the invention, there is also provided a method for the control of monocotyledonous or dicotyledonous weeds on an agricultural or nonagricultural land, which comprises applying to the agricultural or non-agricultural land the N-substituted-3-[(2,3-dimethylmaleimido)amino]benzenesulfonamide derivative of the formula (I) or a herbicidal composition comprising said derivative.

The N-substituted-3-[(2,3-dimethylmaleimido)amino]benzenesulfonamide derivatives of the present invention, which are represented by the formula (I), exhibit reliable herbicidal activity at low application dosages and show selectivity between crops and weeds. The herbicidal compositions of the invention, which contain the above derivatives as effective ingredients, are suitable particularly for controlling before or after germination dicotyledonous and/or monocotyledonous weeds in important crops, for example, such as wheat, rice, corn, soybean, cotton, beet, potato, tomato or the like. They are also usable for the control of weeds not only on agricultural lands such as upland fields, paddy fields and orchards but also on non-agricultural lands such as athletic fields and factory sites.

DETAILED DESCRIPTION OF PREFERRED EMBODIMENTS

Specific examples of the N-substituted-3-[(2,3-dimethylmaleimido)amino]benzenesulfonamide derivative represented by the formula (I) in the invention include those shown in Table 1.

TABLE 1

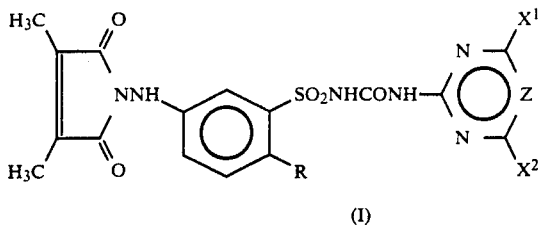

| Compound No. | R | $X^1$ | $X^2$ | Z |
|---|---|---|---|---|
| I-1 | Cl | $OCH_3$ | $OCH_3$ | CH |
| I-2 | $CH_3$ | $OCH_3$ | $OCH_3$ | CH |
| I-3 | $COOCH_3$ | $OCH_3$ | $OCH_3$ | CH |
| I-4 | $COOC_2H_5$ | $OCH_3$ | $OCH_3$ | CH |
| I-5 | $COOCH_3$ | $OCH_3$ | $CH_3$ | N |
| I-6 | $COOC_2H_5$ | $OCH_3$ | $CH_3$ | N |
| I-7 | $COOCH_3$ | $OCH_3$ | $OCH_3$ | N |
| I-8 | $COOC_2H_5$ | Cl | $OCH_3$ | CH |

The N-substituted-3-[(2,3-dimethylmaleimido)amino]benzenesulfonamide derivatives represented by the formula (I) can each be synthesized by reacting a 3-[(2,3-dimethylmaleimido)amino]benzenesulfonamide derivative of the formula (II) and a phenylcarbamate derivative of the following formula (III) in the presence of a base and in an organic solvent in accordance with the following reaction formula:

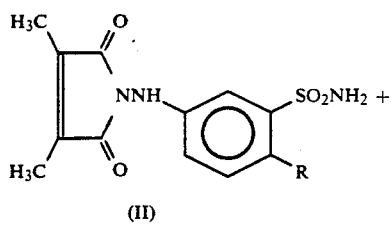

(II)

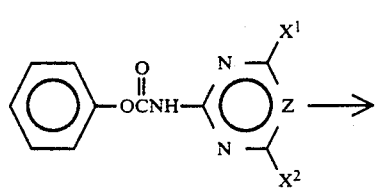

(III)

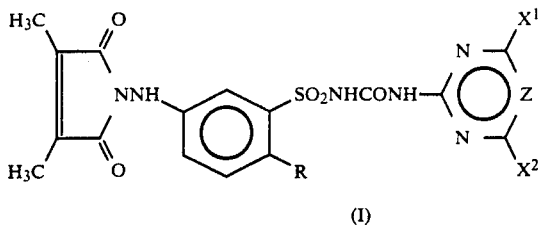

(I)

wherein R, Z, $X^1$ and $X^2$ have the same meanings as defined above.

In the above reaction, dimethylacetamide, N-methylpyrrolidone, acetonitrile or the like can be used as an organic solvent. On the other hand, diazabicyclooctane, diazabicyclononene, diazabicycloundecene or the like can be used as a base.

The reaction is conducted at a temperature in a range of from $-20°$ C. to $100°$ C., preferably from $0°$ C. to $50°$ C. for a reaction period in a range of from 0.5 hour to 24 hours.

After completion of the reaction, the reaction mixture is added to an aqueous solution of dilute hydrochloric acid and the precipitate thus formed is collected by filtration. The precipitate is dried in air and then purified by a purification technique such as reprecipitation or column chromatography or by a washing technique, whereby the intended N-substituted-3-[(2,3-dimethylmaleimido)amino]benzenesulfonamide derivative represented by the formula (I) can be obtained with high purity.

The 3-[(2,3-dimethylmaleimido)amino]benzenesulfonamide derivative represented by the formula (II), which is a preparation intermediate and is employed as the starting material in the above reaction, can be synthesized in accordance with the following reaction formula, using as a starting material a 3-aminobenzenesulfonamide derivative represented by the following formula (IV):

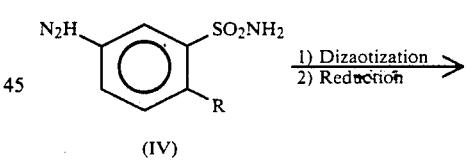

(IV)

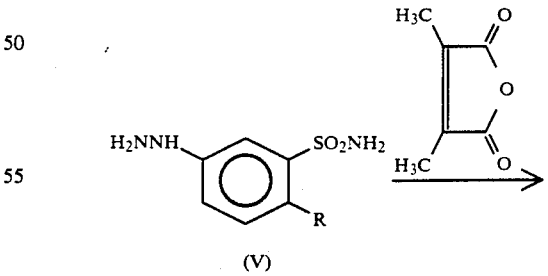

(V)

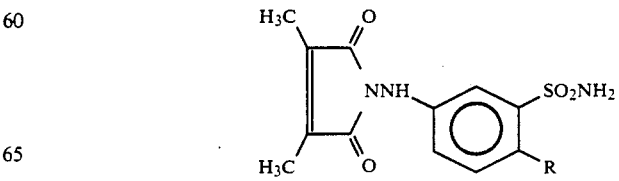

(II)

wherein R has the same meaning as defined above.

Synthesis of the 3-[(2,3-dimethylmaleimido)amino]-benzenesulfonamide derivative represented by the formula (II) can be practiced in the following manner. A 3-hydrazinobenzenesulfonamide derivative represented by the formula (V), which has been obtained by diazotizing the amino group of the compound represented by the formula (IV) and reducing the thus-diazotized derivative, and 2,3-dimethylmaleic anhydride are stirred at 30°–120° C., preferably 70°–90° C. for 0.5–4 hours in acetic acid or propionic acid. After completion of the reaction, the reaction mixture is evaporated to dryness under reduced pressure and the resulting crude product is purified by column chromatography, whereby the 3-[(2,3-dimethylmaleimido)amino]benzenesulfonamide derivative represented by the general formula (II) can be obtained with good purity.

The compound represented by the formula (IV), which was used in the above reaction formula, can be obtained from the corresponding nitrobenzene derivative, for example, by using the process described in Bull. Chem. Soc. Jpn., 55, 3824 (1982); or from the corresponding 3-nitroaniline derivatives, for example, by the process described in Chem. Ber., 90, 841 (1957) or J. Macromol. Sci. Chem., 1969, 941, namely, by synthesizing 3-nitrobenzenesulfonamide derivatives and then reducing the nitro groups into amino groups with $SnCl_2$ in methanol or ethanol containing 35% hydrochloric acid.

Specific examples of the 3-[(2,3-dimethylmaleimido)amino]benzenesulfonamide derivative represented by the formula (II) and useful as a preparation intermediate are summarized in Table 2.

In addition, specific examples of the compound represented by the formula (V) are shown in Table 3.

TABLE 2

| Compound No. | R |
|---|---|
| II-1 | Cl |
| II-2 | $CH_3$ |
| II-3 | $COOCH_3$ |
| II-4 | $COOC_2H_5$ |

TABLE 3

| Compound No. | R |
|---|---|
| V-1 | H |
| V-2 | Cl |
| V-3 | $CH_3$ |
| V-4 | $COOCH_3$ |
| V-5 | $COOC_2H_5$ |

Further, the compound represented by the formula (III) can be obtained from phenyl chloroformate and the corresponding 2-amino-4,6-(di-substituted) pyrimidine (or 1,3,5-triazine), for example, by the process described in European Patent Specification No. 238,070.

The N-substituted-3-[(2,3-dimethylmaleimido)amino]benzenesulfonamide derivatives exhibit reliable herbicidal activity at low application dosages and show selectivity between crops and weeds. The herbicidal compositions of the invention, which contain the above compounds as effective ingredients, are therefore suitable for controlling either before or after emergence monocotyledonous weeds and/or dicotyledonous weeds in important crops such as wheat, rice, corn, soybean, cotton, beet, potato and tomato.

Exemplary dicotyledonous weeds which can be controlled by the herbicides of the invention include Amaranthus, Bidens, Stellaria, Solanum, Abutilon, Convolvulus, Matricaria, Galium, Lindernia, etc.

Illustrative monocotyledonous weeds include Echinochloa, Setaria, Digitaria, Avena, Cyperus, Alisma, Monochoria, etc.

The herbicides of the invention may take any preparation forms such as wettable powder, emulsion, powder, granule and the like. Known agronomically-acceptable vehicles (diluents) and aids can be used.

The applicable places of the herbicides according to the invention range from agricultural lands such as upland fields, paddy fields and orchard to non-agricultural lands such as athletic fields and factory sites.

EXAMPLES

The present invention will hereinafter be described by the following examples.

SYNTHESIS EXAMPLE 1

Synthesis of ethyl 4-(2,5-dihydro-3,4-dimethyl-2,5-dioxo-1H-pyrrol-1-yl)amino]-2-[(4,6-dimethoxypyrimidin-2-yl)aminocarbonylaminosulfonyl]benzoate (Compound No. I-4)

At room temperature, 158 mg (0.43 mmol) of ethyl 2-(aminosulfonyl)-4-[(2,5-dihydro-3,4-dimethyl-2,5-dioxo-1H-pyrrol-1-yl)amino]benzoate and 118 mg (0.43 mmol) of phenyl (4,6-dimethoxypyrimidin-2-yl)carbamate were dissolved in 1.5 ml of N,N-dimethylacetamide. Then, 73 mg of 1,8-diazabicyclo[5.4.0]undec-7-ene were added, followed by stirring for 5 minutes. The resultant mixture was allowed to stand for 15 hours. Thereafter, 0.2 ml of 35% hydrochloric acid was added to 20 ml of ice water, followed by the addition of the reaction mixture in 0.2 ml portions under stirring. After the reaction mixture was stirred for 20 minutes, the resulting precipitate was collected by filtration and dried in air. Using dichloromethane as an eluent, the crude product was purified by chromatography on a column of silica gel ("WAKO GEL C-300", trade name; product of Wako Pure Chemical Industries, Ltd.). Yield: 162 mg (58%). Melting point: 121°–123° C. (decomposed). Its physicochemical properties are shown in Table 4.

SYNTHESIS EXAMPLE 2

Synthesis of methyl 4-[(2,5-dihydro-3,4-dimethyl-2,5-dioxo-1H-pyrrol-1-yl)amino]-2-(4,6dimethoxy1,3,5-triazin-2-yl)aminocarbonyl]benzoate (Compound No. I-7)

At room temperature, 172 mg (0.5 mmol) of methyl 2-(aminosulfonyl)-4-[(2,5-dihydro-3,4-dimethyl-2,5-dioxo-1H-pyrrol-1-yl)amino]benzoate and 138 mg (0.5 mmol) of phenyl (4,6-dimethoxy-1,3,5-triazin-2-yl)carbamate were dissolved in 1.5 ml of N,N-dimethylacetamide. Then, 76 mg of 1,8-diazabicyclo[5.4.0]undec-7-ene were added, followed by stirring for 5 minutes. The resultant mixture was allowed to stand for 6 hours. Thereafter, 0.2 ml of 35% hydrochloric acid was added to 20 ml of ice water, followed by the addition of the reaction mixture in 0.2 ml portions under stirring. After the reaction mixture was stirred for 20 minutes, the resulting precipitate was collected by filtration and dried in air. Using a 1:2 mixed solvent of methyl acetate and benzene as an eluent, the crude product was purified by chromatography on a column of silica gel ("WAKO GEL C-300", trade name; product of Wako Pure Chemical Industries, Ltd.). Yield: 59 mg (22%). Melting point: 123°–127° C. Its physicochemical properties are shown in Table 4.

The other N-substituted-3-[(2,3-dimethylmaleimido)amino]benzenesulfonamide derivatives shown in Table 1 were also synthesized in a similar manner to Synthesis Example 1. Namely, after obtaining crude products by a similar procedure to Synthesis Example 1, they were separately purified by chromatography on a silica gel column, reprecipitation or washing. Physicochemical properties of each of the N-substituted-3-[(2,3-dimethylmaleimido)-amino]benzenesulfonamide derivatives are shown in Table 4. Incidentally, in Table 4 and Table 6 which will be given subsequently, the abbreviations in the columns for NMR data have the following meanings:

δ: (ppm), s: singlet, d: doublet, t: triplet,
q: quartet, m: multiplet, dd: double doublet,
br: broad.

Further, with respect to the individual N-substituted-3-[(2,3-dimethylmaleimido)amino]benzenesulfonamide derivatives, the solvents employed upon purification thereof and the yields attained were as follows:

Compounds purified by reprecipitation:

| Compound No. | Solvent employed | Yield (%) |
| --- | --- | --- |
| I-1 | $CH_2Cl_2$ + petroleum ether | 38 |
| I-2 | $CH_2Cl_2$ + petroleum ether | 75 |

Compounds purified by washing:

| Compound No. | Solvent employed | Yield (%) |
| --- | --- | --- |
| I-3 | petroleum ether | 40 |

Compounds purified by column chromatography:

| Compound No. | Solvent employed | Yield (%) |
| --- | --- | --- |
| I-4 | $CH_2Cl_2$ | 58 |
| I-5 | methyl acetate + benzene | 22 |
| I-6 | ethyl acetate + benzene | 21 |
| I-7 | methyl acetate + benzene | 22 |
| I-8 | ethyl acetate + benzene | 64 |

TABLE 4

| Compound No. | MS(m/e) (A)* | MS(m/e) (B)** | Melting Point or Decomposition Point (°C.) | IR (KBr, cm$^{-1}$) | NMR (δ) CDCl$_3$ |
|---|---|---|---|---|---|
| I-1 | 355 | 155 | 142–144 Decomposition | 3200–2600,1720,1610,1580,1450, 1370,1360,1200,1170,590,520 | 2.006(6H,s) 3.913(6H,s) 5.751(6H,s) 6.234(1H,s) 6.810(1H,dd,8.54Hz,2.44Hz) 7.218(1H,s) 7.277(1H,d,8.54Hz) 7.665(1H,d,2.44Hz) 12.877(1H,s) |
| I-2 | 335 | 155 | 120–122 Decomposition | 3420br,2940,1780,1720,1610, 1580,1490,1450,1370,1350,1220, 1200,1170,590 | 2.040(6H,s) 2.560(3H,s) 3.939(6H,s) 5.780(1H,s) 6.051(1H,s) 6.846(1H,dd,8Hz,1.5Hz) 7.147(1H,d,8Hz) 7.198(1H,s) 7.645(1H,d,1.5Hz) 12.611(1H,s) |
| I-3 | 379 | 155 | 136–139 Decomposition | 3400–2700br,3300,2940,1780, 1720,1600,1570,1490,1440,1370, 1350,1270,1240,1220,1190,1160, 1120,1090,1050,820,770,750, 630,580,530,510 | 2.057(6H,s) 3.822(3H,s) 4.005(6H,s) 5.773(1H,S) 6.576(1H,s) 6.829(1H,dd,8Hz,1.5Hz) 7.367(1H,s) 7.666(1H,d,8Hz) 7.797(1H,d,1.5Hz) 12.523(1H,s) |
| I-4 | 393 | 155 | 121–123 Decomposition | 3380–2700,3320,1780,1710,1600, 1570,1490,1440,1350,1270,1240, 1220,1190,1170,1120,580 | 1.318(3H,t,7.33Hz) 2.055(6H,s) 4.011(6H,s) 4.274(2H,q,7.33Hz) 5.768(1H,s) 6.610(1H,s) 6.832(1H,dd,8.55Hz,2.44Hz) 7.384(1H,s) 7.660(1H,d,8.55Hz) 7.792(1H,d,2.44Hz) 12.503(1H,s) |
| I-5 | 379 | 140 | 123–127 Decomposition | 3330,3200–2800,1790,1730,1610, 1560,1490,1450,1360,1270,1160, 1120,820,590 | 2.052(6H,s) 2.626(3H,s) 3.874(3H,s) 4.088(3H,s) 6.828(1H,dd,8.55Hz,2.44Hz) 6.881(1H,s) 7.684(1H,d,8.55Hz) 7.797(1H,d,2.44Hz) 8.145br(1H,s) 12.405br(1H,s) |
| I-6 | 393 | 140 | 123–126 Decomposition | 3330,3200–2800,1790,1730,1610, 1570,1490,1450,1370,1270,1250, 1170,820,590 | 1.349(3H,t,7.32Hz) 2.052(6H,s) 2.616(3H,s) 4.084(3H,s) 4.326(2H,q,7.32Hz) 6.771(1H,s) 6.830(1H,dd,8.55Hz,2.45Hz) 7.684(1H,d,8.55Hz) 7.782(1H,d,2.45Hz) 7.995br(1H,s) 12.435br(1H,s) |
| I-7 | 379 | 156 | 123–127 Decomposition | 3330,3200–2800,1790,1730,1610, 1570,1490,1450,1380,1350,1270, 1240,1170,1150,820,590 | 2.050(6H,s) 3.876(3H,s) 4.101(6H,s) 6.793(1H,s) 6.835(1H,dd,8.55Hz,2.44Hz) 7.682(1H,d,2.44Hz) 7.789(1H,d,8.55Hz) 8.007(1H,s) 12.120(1H,s) |
| I-8 | 393 | 159 | 118–122 Decomposition | 3330,3200–2800,1790,1730,1610, 1590,1570,1500,1450,1360,1330, 1270,1250,1170,1120,590 | 1.335(3H,t,7.33Hz) 2.052(6H,s) 4.135(6H,s) 4.302(2H,q,7.33Hz) 6.469(1H,s) 6.698(1H,s) 6.835(1H,dd,8.55Hz,2.44Hz) 7.682(1H,d,8.55Hz) 7.792(1H,d,2.44Hz) 7.797(1H,s) 12.037(1H,s) |

*(A)

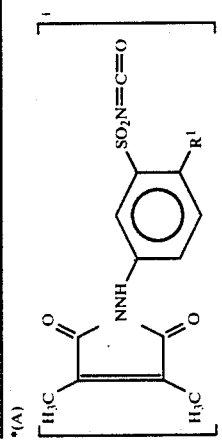

**(B)

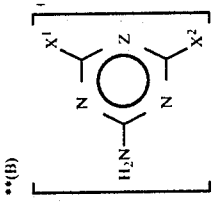

SYNTHESIS EXAMPLE 3

Synthesis of preparation intermediate, ethyl 2-(aminosulfonyl)-4-[(2,5-dihydro-3,4-dimethyl-2,5-dioxo-1H-pyrazol-1-yl)amino]benzoate (Compound No. II-4)

(1) Synthesis of ethyl 2-(aminosulfonyl)-4-hydrazinobenzoate (Compound No. V-5)

Ethyl 4-amino-2-(aminosulfonyl)benzoate (2.44 g; 10 mmol) was finely ground and then added to a mixture of 5 ml of 35% hydrochloric acid and 5 ml of water. The mixture thus prepared was stirred for 5 minutes at room temperature. It was thereafter cooled with ice water and under stirring, a solution of 0.72 g (10.5 mmol) of sodium nitrite in 3 ml of water was added over 3 minutes to conduct diazotization.

In 5 ml of 35% hydrochloric acid, 5.2 g (27.4 mmol) of stannous chloride were dissolved. The resulting solution was cooled with ice water and stirred, followed by the addition of the diazotized compound prepared above.

After the resultant mixture was stirred for 20 minutes, it was left over for 15 hours in a refrigerator. The reaction mixture was then transferred into a 2-l beaker, to which 28 g of sodium bicarbonate powder were then added under stirring to adjust the pH to 6. The mixture thus prepared was then extracted twice with 700 ml of ethyl acetate. The extract was dried over sodium sulfate, and ethyl acetate was distilled off to obtain a pale brown solid. Yield: 2.66 g (98%). Melting point: 122°–124° C. (decomposed). Its physicochemical properties are shown in Table 6.

(2) Synthesis of ethyl 2-(aminosulfonyl)-4-[(2,5-dihydro-3,4-dimethyl-2,5-dioxo-1H-pyrrol-1-yl)aminobenzoate (Compound No. II-4)

The compound synthesized in the above procedure (1) [Compound No. V-5; 259 mg (1 mmol)] and 132.6 mg (1 mmol) of 2,3-dimethylmaleic anhydride were dissolved at room temperature in 4 ml of acetic acid, followed by stirring at 80°–90° C. for 3 hours. The reaction mixture was then evaporated to dryness under reduced pressure. Using dichloromethane as an eluent, the crude reaction product thus obtained was purified by chromatography on a column of silica gel ("WAKO GEL C-300", trade name; product of Wako Pure Chemical Industries, Ltd.). Yield: 203.8 mg (55%). Melting point: 184°–186° C. Its physicochemical properties are shown in Table 5.

In addition, physicochemical properties of the other compounds of the formula (II) synthesized in a similar manner to the above-described procedure are also shown in Table 5.

Further, physicochemical properties of other preparation intermediates synthesized in a similar manner to the above procedure (1) are also shown in Table 6.

TABLE 5

| Compound No. | Yield (%) | MS (m/e) M+ | Melting Point or Decomposition Point (°C.) | IR (KBr, cm$^{-1}$) |
|---|---|---|---|---|
| II-1 | 67 | 329 | 216–221 | 3370, 3320, 3270, 1780, 1730, 1600, 1550, 1470, 1340, 1175, 1165, 590, |
| II-2 | 62 | 309 | 109–111 Decomposed | 3370, 3320, 3260, 1770, 1710, 1600, 1480, 1320, 1310, 1150, 1130, 1080, 1050, 920, 680, 590, 510 |
| II-3 | 47 | 353 | 120–125 | 3320br, 2950, 1780, 1720, 1600, 1430, 1340, 1310, 1280, 1250, 1170, 1120, 1090, 1050, 930, 770, 710, 700, 590, 510 |
| II-4 | 55 | 367 | 184–186 | 3380, 3250, 2980, 1780, 1720, 1700, 1600, 1420, 1320, 1290, 1270, 1240, 1160, 1130, 1090, 1050, 780, 700, 600, 520 |

TABLE 6

| Compound No. | Yield (%) | MS (m/e) M+ | Melting Point or Decomposition Point (°C.) | IR (KBr, cm$^{-1}$) | NMR (δ) |
|---|---|---|---|---|---|
| V-1 | 89 | 187 | 113–116 | 3360, 3350, 3300, 3220, 1600, 1470, 1340, 1330, 1290, 1140, 1090, 780, 680, 580, 510 | |
| V-2 | 84 | 221 | 155–158 Decomposed | 3370, 3330, 3130, 2970, 1590, 1560, 1460, 1330, 1270, 1160, 970, 830, 740, 690, 590, 550, 510 | |
| V-3 | 83 | 201 | 161–164 | 3300, 3250, 3010, 1610, 1490, 1300, 1160, 1140, 920, 820, 690, 600, 520 | d$_6$-DMSO:2.409(3H,s) 4.025br(2H,s) 6.840 (1H,dd,8.5 Hz,1.8 Hz) 6.901(1H,s) 7.048(1H, d,8.5 Hz) 7.148(2H,s) 7.349(1H,d,1.8 Hz) |
| V-4 | 86 | 245 | 168–170 | 3350, 3310, 3250, 1680, 1630, 1590, 1440, 1350, 1330, 1300, 1270, 1170, 1160, 780, 700, 600 | |
| V-5 | 98 | 259 | 122–124 Decomposed | 3320, 3270, 2980, 1700, 1590, 1370, 1320, 1300, 1270, 1250, 1150, 1120, 770, 740, 700 | |

Compounds obtained in a similar manner to Synthesis Examples 1 and 2 are shown in Table 7.

TABLE 7

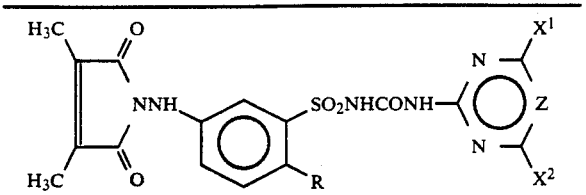

| Compound No. | R | X¹ | X² | Z |
|---|---|---|---|---|
| I-9 | COOCH₃ | OCH₃ | OCH₃ | N |
| I-10 | Cl | OCH₃ | CH₃ | N |
| I-11 | Cl | OCH₃ | OCH₃ | N |
| I-12 | CH₃ | OCH₃ | CH₃ | N |
| I-13 | CH₃ | OCH₃ | OCH₃ | N |
| I-14 | Cl | OCH₃ | CH₃ | CH |
| I-15 | Cl | CH₃ | CH₃ | CH |
| I-16 | COOCH₃ | OCH₃ | CH₃ | CH |
| I-17 | COOCH₃ | CH₃ | CH₃ | CH |
| I-18 | CH₃ | CH₃ | CH₃ | CH |

Formulation examples and tests will hereinafter be described. It should be borne in mind that the vehicles (diluents) and aids, their mixing ratios and effective components can vary in wide ranges, respectively.

Formulation Example 1: Wettable Powder

| | |
|---|---|
| Compound (Compound No. I-4) | 50 parts |
| A salt of ligninsulfonic acid | 5 parts |
| A salt of alkylsulfonic acid | 3 parts |
| Diatomaceous earth | 42 parts |

The above ingredients are mixed and ground into a wettable powder. For application, it is diluted with water.

Formulation Example 2: Emulsion

| | |
|---|---|
| Compound (Compound No. I-5) | 25 parts |
| Xylene | 65 parts |
| Polyoxyethylene alkylaryl ether | 10 parts |

The above ingredients are mixed intimately into an emulsion. For application, it is diluted with water.

Formulation Example 3: Granule

| | |
|---|---|
| Compound (Compound No. I-7) | 8 parts |
| Bentonite | 40 parts |
| Clay | 45 parts |
| A salt of ligninsulfonic acid | 7 parts |

The above ingredients are mixed intimately and after the addition of water, were kneaded and then formed into granules by an extruding granulator. They were then dried to provide a granular formulation, namely, a granule.

Test 1: Test on Herbicidal Activity by Foliar Application

Herbicidal solutions of each test compound, which had been prepared by dissolving at predetermined concentrations such a wettable powder of the test compound as that described in the above formulation example, and sprayed at dosages of 10 g/ha and 100 g/ha over foliar parts of *Amaranthus retroflexus* (Redroot pigweed), *Bidens pilosa* (Common blackjack), *Sinapis arvensis* (Wild mustard), *Stellaria media* (Common chickweed), *Cassia obtusifolia* (Sicklepod), *Solanum nigrum* (Black nightshade), *Abutilon theophrasti* (Velvetleaf), *Convolvulus arvensis* (Field bindweed), *Matricaria chamomilla* (Wild chamomile), *Setaria viridis* (Green foxtail), *Echinochloa frumentaceum* (Barnyard grass), *Avena fatua* (Wild oat), and *Digitaria adscendens* (Henry crabgrass) which had been allowed to grow individually to 2-4 leaf stage in pots. Fourteen days later after spraying of the test compound, its herbicidal activity was evaluated in accordance with the below-described system. The results are summarized in Table 8.

Ranking system:

Herbicidal activity

0: No effects
1: less than 30% of total kill
2: 30% (inclusive)—50% (exclusive) of total kill
3: 50% (inclusive)—70% (exclusive) of total kill
4: 70% (inclusive)—90% (exclusive) of total kill
5: 90% (inclusive)—100% (inclusive) of total kill

TABLE 8

| Compound No. | Amount (g/ha) | A.r. | B.p. | S.a. | S.m. | C.o. | S.n. | A.t. | C.a. | M.c. | S.v. | E.f. | A.f. | D.a. |
|---|---|---|---|---|---|---|---|---|---|---|---|---|---|---|
| I-1 | 10 | 5 | 3 | 5 | 5 | 3 | 2 | 5 | 1 | 5 | 2 | 2 | 5 | 4 |
| | 100 | 5 | 5 | 5 | 5 | 5 | 5 | 5 | 5 | 5 | 5 | 5 | 5 | 5 |
| I-2 | 10 | 5 | 3 | 5 | 5 | 4 | 4 | 5 | 2 | 1 | 1 | 1 | 1 | 0 |
| | 100 | 5 | 5 | 5 | 5 | 5 | 5 | 5 | 3 | 5 | 3 | 3 | 5 | 3 |
| I-3 | 10 | 5 | 3 | 5 | 5 | 1 | 5 | 3 | 3 | 5 | 1 | 2 | 1 | 1 |
| | 100 | 5 | 5 | 5 | 5 | 5 | 5 | 5 | 5 | 5 | 5 | 5 | 5 | 5 |
| I-4 | 10 | 5 | 5 | 5 | 5 | 5 | 5 | 5 | 5 | 5 | 4 | 2 | 5 | 2 |
| | 100 | 5 | 5 | 5 | 5 | 5 | 5 | 5 | 5 | 5 | 5 | 5 | 5 | 5 |
| I-5 | 10 | 4 | 5 | 5 | 5 | 1 | 1 | 5 | 3 | 5 | 2 | 1 | 1 | 1 |
| | 100 | 5 | 5 | 5 | 5 | 5 | 5 | 5 | 4 | 5 | 4 | 4 | 3 | 4 |
| I-6 | 10 | 5 | 5 | 5 | 5 | 2 | 5 | 5 | 4 | 5 | 3 | 3 | 3 | 1 |
| | 100 | 5 | 5 | 5 | 5 | 4 | 5 | 5 | 5 | 5 | 3 | 5 | 5 | 2 |
| I-7 | 10 | 4 | 4 | 5 | 5 | 2 | 5 | 5 | 3 | 5 | 3 | 2 | 3 | 1 |
| | 100 | 5 | 5 | 5 | 5 | 5 | 5 | 5 | 5 | 4 | 5 | 5 | 5 | 3 |
| I-8 | 10 | 5 | 4 | 5 | 5 | 3 | 4 | 5 | 4 | 5 | 2 | 2 | 2 | 2 |

TABLE 8-continued

| Compound No. | Amount (g/ha) | A.r. | B.p. | S.a. | S.m. | C.o. | S.n. | A.t. | C.a. | M.c. | S.v. | E.f. | A.f. | D.a. |
|---|---|---|---|---|---|---|---|---|---|---|---|---|---|---|
| | 100 | 5 | 5 | 5 | 5 | 4 | 5 | 5 | 5 | 5 | 4 | 4 | 5 | 3 |

(Note)
A.r.: Amaranthus retroflexus
B.p.: Bidens pilosa
S.a.: Sinapis arvensis
S.m.: Stellaria media
C.o.: Cassia obtusifolia
S.n.: Solanum nigrum
A.t.: Abutilon theophrasti
C.a.: Convolvulus arvensis
M.c.: Matricaria chamomilla
S.v.: Setaria viridis
E.f.: Echinochloa frumentaceum
A.f.: Avena fatua
D.a.: Digitaria adscendens

TEST 2: GERMINATION TEST OF SEEDS

Two sheets of filter paper were placed in a superposed relation in each of Petri dishes having a diameter of 9 cm. Water suspensions of each test compound (concentrations of the active ingredient: 1 ppm and 50 ppm) were separately poured in an amount of 5 ml per dish into the Petri dishes. Seeds of *Amaranthus retroflexus* (Redroot pigweed), *Bidens pilosa* (Common blackjack), *Matricaria chamomilla* (Wild chamomile), *Solanum nigrum* (Black nightshade), *Echinochloa oryzicola* (Barnyard grass), *Cyperus iria* (Rice flatsedge) and *Setaria viridis* (Green foxtail) were placed at a rate of 10 seeds per dish in the Petri dishes. They were therafter allowed to germinate in a constant-temperature chamber at 28° C. Fourteen days later after placement in the Petri dishes, the degrees of germination and growth inhibition were observed visually. The observation results were ranked in accordance with the below-described 6-stage system. The results are summarized in Table 9.

Growth inhibition rate

0: No inhibition
1: less than 30%
2: 30% (inclusive)—50% (exclusive)
3: 50% (inclusive)—70% (exclusive)
4: 70% (inclusive)—90% (exclusive)
5: 90% (inclusive)—100% (exclusive)

TABLE 9

| Compound No. | Concentration (ppm) | A.r. | B.p. | M.c. | S.n. | E.o. | C.i. | S.v. |
|---|---|---|---|---|---|---|---|---|
| I-1 | 1 | 3 | 0 | 3 | 3 | 2 | 4 | 2 |
|  | 50 | 4 | 3 | 4 | 3 | 4 | 4 | 4 |
| I-2 | 1 | 4 | 4 | 5 | 3 | 4 | 4 | 5 |
|  | 50 | 4 | 4 | 5 | 4 | 5 | 4 | 5 |
| I-3 | 1 | 3 | 1 | 3 | 0 | 1 | 1 | 1 |
|  | 50 | 4 | 5 | 4 | 3 | 5 | 5 | 5 |
| I-4 | 1 | 4 | 4 | 5 | 5 | 4 | 4 | 5 |
|  | 50 | 5 | 4 | 5 | 5 | 5 | 5 | 5 |
| I-5 | 1 | 0 | 1 | 2 | 1 | 0 | 1 | 1 |
|  | 50 | 3 | 4 | 5 | 4 | 3 | 4 | 4 |
| I-6 | 1 | 3 | 0 | 1 | 3 | 0 | 1 | 1 |
|  | 50 | 4 | 3 | 5 | 4 | 2 | 4 | 4 |
| I-7 | 1 | 2 | 0 | 1 | 1 | 0 | 1 | 0 |
|  | 50 | 4 | 3 | 5 | 4 | 2 | 4 | 3 |
| I-8 | 1 | 3 | 1 | 1 | 3 | 1 | 0 | 1 |
|  | 50 | 4 | 4 | 5 | 3 | 4 | 3 | 5 |

(Note)
A.r.: Amaranthus retroflexus
B.p.: Bidens pilosa
M.c.: Matricaria chamomilla
S.n.: Solanum nigrum
E.o.: Echinochloa oryzicola
C.i.: Cyperus iria
S.v.: Setaria viridis

We claim:

1. An N-substituted-3-[(2,3-dimethylmaleimido)-amino]benzenesulfonamide derivative of the formula (I):

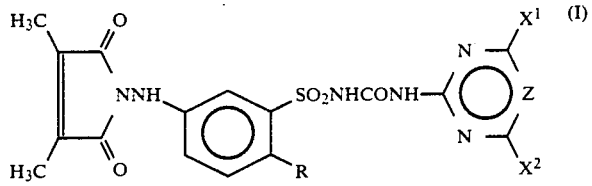

wherein R is Cl, $C_1-C_3$ alkyl or $C_1-C_4$ alkoxycarbonyl; Z is CH, $X^1$ is Cl or $C_1-C_3$ alkoxyl; and $X^2$ is $C_1-C_3$ alkyl or $C_1-C_3$ alkoxyl.

2. A derivative of claim 1, wherein, R is Cl, $CH_3$, $COOCH_3$ or $COOC_2H_5$, $X^1$ is Cl or $OCH_3$, and $X^2$ is $OCH_3$.

3. A derivative of claim 1, wherein R is $COOCH_3$ or $COOC_2H_5$, $X^1$ is $OCH_3$, and $X^2$ is $CH_3$ or $OCH_3$.

4. A herbicidal composition comprising a herbicidally effective amount of an N-substituted-3-[(2,3-dimethylmaleimido)amino]benzenesulfonamide derivative of claim 1 and an agronomically-acceptable vehicle or diluent.

5. A method for the control of monocotyledonous or dicotyledonous weeds on an agricultural or non-agricultural land, which comprises applying to the agricultural or non-agricultural land an N-substituted-3-[(2,3-dimethylmaleimido)amino]benzenesulfonamide derivative of claim 1 or a herbicidal composition comprising said derivative.

* * * * *